(12) United States Patent
Sarmala et al.

(10) Patent No.: US 8,951,416 B2
(45) Date of Patent: Feb. 10, 2015

(54) SEPARATION PROCESS

(75) Inventors: Päivi Sarmala, Rajamäki (FI); Hannu Paananen, Kantvik (FI); Pia Saari, Espoo (FI); Kati Kekäläinen, Espoo (FI); Jarmo Kuisma, Lohja (FI)

(73) Assignee: Dupont Nutrition Biosciences APS, Copenhagen K (DK)

( * ) Notice: Subject to any disclaimer, the term of this patent is extended or adjusted under 35 U.S.C. 154(b) by 826 days.

(21) Appl. No.: 13/202,613

(22) PCT Filed: Feb. 24, 2010

(86) PCT No.: PCT/FI2010/050133
§ 371 (c)(1),
(2), (4) Date: Sep. 22, 2011

(87) PCT Pub. No.: WO2010/097513
PCT Pub. Date: Sep. 2, 2010

(65) Prior Publication Data
US 2012/0010429 A1    Jan. 12, 2012

Related U.S. Application Data

(60) Provisional application No. 61/155,261, filed on Feb. 25, 2009.

(51) Int. Cl.
*C13B 20/14* (2011.01)
*B01D 15/36* (2006.01)
*B01D 15/18* (2006.01)
*C13K 13/00* (2006.01)

(52) U.S. Cl.
CPC ............. *C13B 20/14* (2013.01); *B01D 15/185* (2013.01); *B01D 15/362* (2013.01); *B01D 15/363* (2013.01); *C13K 13/00* (2013.01)
USPC ............................ 210/656; 562/554; 562/575

(58) Field of Classification Search
CPC .......... B01D 15/36; B01D 15/18; C13D 3/14
USPC ..................... 210/656; 562/554, 575
See application file for complete search history.

(56) References Cited

U.S. PATENT DOCUMENTS

| | | |
|---|---|---|
| 4,843,156 A | 6/1989 | Miyake et al. |
| 5,177,008 A | 1/1993 | Kampen |
| 5,730,877 A | 3/1998 | Heikkila et al. |
| 6,331,250 B1 | 12/2001 | Kaneko et al. |
| 6,770,757 B2 | 8/2004 | Paananen et al. |
| 6,896,811 B2 | 5/2005 | Heikkila et al. |

FOREIGN PATENT DOCUMENTS

| | | |
|---|---|---|
| JP | 2004-509932 A | 4/2004 |
| JP | 2004-533919 A | 11/2004 |
| WO | 97/45185 A1 | 12/1997 |
| WO | WO 2007/080228 A1 | 7/2007 |

OTHER PUBLICATIONS

International Search Report dated Jun. 8, 2010, issued in PCT/FI2010/050133.
Notice of Reasons for Rejection issued in Japanese Patent Application No. 2011-551506, dated Jul. 2, 2014 (iEnglish translation and Japanese translation).

*Primary Examiner* — Yevegeny Valenrod
(74) *Attorney, Agent, or Firm* — Scully, Scott, Murphy & Presser, P.C.

(57) ABSTRACT

The present invention relates to a method of separating betaine and at least one other component from a sugar beet based fermentation solution. The invention is based on the use of a combination of SAC resins and WAC resins in a specific order and in specified proportions in a chromatographic SMB separation system. The chromatographic separation system is preferably a single integrated SMB system comprising both SAC and WAC resin beds.

35 Claims, 2 Drawing Sheets

SEPARATION PROCESS

CROSS-REFERENCE TO RELATED APPLICATIONS

This application claims the benefit of U.S. Provisional Application No. 61/155,261 filed on Feb. 25, 2009.

FIELD OF THE INVENTION

The present invention relates to the field of recovering betaine from sugar beet based sources. Especially, the invention relates to a chromatographic SMB method of separating betaine and at least one other component from a sugar beet based fermentation solution, such as vinasse. The other component to be separated may be glycerol, for example.

BACKGROUND OF THE INVENTION

U.S. Pat. No. 5,177,008 (W. H. Kampen) discloses a continuous process for recovering glycerol and betaine from a stillage product, which is obtained as a by-product from the fermentation and distillation of sugar beets (molasses) in the production of ethanol. The process comprises a first chromatographic separation of the clarified stillage with an ion-exclusion system for separating glycerol and betaine as a mixture, followed by concentration of the mixture and subsequent second chromatographic separation of the mixture into betaine and glycerol with a second ion-exlusion system. In accordance with Example 8, the first chromatographic separation is carried out with a strong acid cation exchange resin in potassium form and the second chromatographic separation is carried out with a polystyrene strong base anion exchange gel resin in sulfate form. It is recited that the process provides a glycerol stream with a purity of 97.6% (after further purification with mixed-bed ion exchange) and a betaine stream with a purity of 88.2%. The overall recovery was 88.5% for glycerol and 93.2% for betaine.

U.S. Pat. No. 5,730,877 (Xyrofin Oy) relates to a chromatographic simulated moving bed method of fractionating a solution in a separation system comprising different ion forms (a divalent cation form and a monovalent cation form). Example 4 discloses a three-column separation of vinasse with a strong acid cation exchange resin. Columns 1 and 2 (in stages 1 and 2) were in $K^+$ form and column 3 (in stage 3) was in $Ca^{2+}$ form. It is also recited that there was a pH adjustment unit between columns 2 and 3. A betaine fraction, a glycerol fraction, an inositol fraction, and a residual fraction are recovered. The content of betaine in the betaine fraction was 77.6%.

U.S. Pat. No. 6,331,250 B1 (Organo Corporation) discloses a chromatographic separation process for separating at least three components from a solution in a separation system comprising at least two different packing materials for regulating the resolution of the components. The packing materials are preferably strongly acid cation exchange resins, one of which is in a monovalent ion form and the other is in a bivalent ion form. The process may be carried out batchwise or as a simulated moving bed process. In Example 1, a solution containing disaccharides, glucose, fructose, and betaine was separated in a 10-column system, where five columns were in $Ca^{2+}$ form and five columns were in $Na^+$ form. A glucose/fructose fraction and a betaine fraction were collected. The betaine fraction had a purity of 99.4%. Betaine recovery into the betaine fraction was 96.8%.

U.S. Pat. No. 6,770,757 B2 (Finnfeeds Finland Oy) discloses a multistep process for recovering one or more products, such as betaine, from beet derived solutions with weakly acid cation exchange resins (WAC), which, according to the examples, were in $Na^+$ form. The sugar beet based solution used as a starting material may be vinasse, molasses or betaine molasses, for example. The pH of the WAC separation is optionally adjusted to a range of 6 to 11, preferably 9 to 11. The multistep process may also comprise a separation step with a strongly acid cation exchange resin (SAC), either before or after the WAC separation.

WO 2007/080228 A1 (Finnfeeds Finland Oy) discloses a method of chromatographic separation of betaine from a sugar beet based solution by using a weakly acid cation exchange resin (WAC) in $H^+$ form. The sugar beet based solution used as the starting material may be the same as above. In addition to betaine, for example inositol and/or glycerol may be recovered. The separation is typically effected at a pH below 6, preferably between 1.4 and 5.1. It also appears that the retention factor of betaine may be controlled by pH adjustment so that the elution of betaine is retarded by decreasing the pH. Furthermore, it is recited that the WAC separation may be combined with an additional chromatographic separation, which may be carried out for example with a strongly acid cation exchange resin (SAC). In one embodiment of the method, the SAC separation is carried out first and the WAC separation thereafter.

The prior art processes described above have several drawbacks. Owing to the inefficient fractionation processes with several separation unit operations, intermediate evaporations are required between the unit operations. Furthermore, it was found that SAC resins in monovalent ion form ($Na^+$) in the separation of vinasse did not separate glycerol from betaine. The purity of the betaine fraction was poor. On the other hand, a combination of monovalent SAC resins in alkali metal form and divalent SAC resins separated glycerol and betaine, but in a long term use resulted in incomplete separation of salts from betaine, because ions from the $Na^+$ column migrated into the $Ca^{2+}$ column and vice versa. Consequently, the columns must be frequently regenerated, which increases the amount of waste effluents and causes interruptions in production.

As to the separation of betaine with monovalent WAC resins, it was found that practically very poor separation of color from betaine took place and that salts eluted as undulating peaks. Furthermore, especially $H^+$ form resins have the drawback that a strong tailing effect is associated with the betaine peak, which leads to broadening of the betaine peak. Tailing decreases the separation capacity and concentration of fractions, leading to increased energy consumption in evaporation. WAC resins in the separation of betaine are also problematic in that they require a specific pH range for long term operation, depending on the ion form of the resin. For example, the $H^+$ form resin as a rule requires a feed pH lower than 4.5 and the $Na^+$ form resin as a rule requires a feed pH higher than 7.5. On the other hand, in order for the WAC resin in $Na^+$ form to be stable, a pH higher than 9 is generally required. Since vinasse has a pH of approximately 5 to 6, considerable amounts of pH adjustment chemicals are necessary for industrial operation of the WAC resins.

DEFINITIONS RELATING TO THE INVENTION

"A separation profile" refers to a dry solids profile formed on account of the feed of an eluent and the components of the feed solution and the flow through the packing material bed in a separation column, obtained by accomplishing/repeating a separation sequence.

"A part of the separation profile" refers to a section of the separation profile. In connection with the present invention, a part of the separation profile refers especially to a part of the separation profile enriched in betaine and at least one other component.

"A retention volume" is the volume required to elute a certain point of the separation profile through the column. In connection with the present invention, the retention volume especially refers to the volume required to elute the start of a component peak (such as a betaine or salt peak) through the column.

"A sequence" or "a separation sequence" is a predetermined sequence of steps in a sequential chromatographic separation process, comprising all steps that are needed to facilitate the separation of feed components to product fraction(s) or other fractions.

"A feed" is an amount of feed solution introduced to the separation column during one sequence.

"A step" comprises one or more of a feeding phase, an elution phase, and a circulation phase.

During the feeding phase, a feed solution, and possibly also an eluent during a simultaneous eluting phase, is introduced into a predetermined partial packed bed or predetermined partial packed beds. During the feeding phase, and/or one or more other phases, one or more product fractions can be withdrawn.

During the elution phase, an eluent is fed into predetermined partial packed beds.

During the circulation phase, essentially no feed solution or eluent is supplied to the partial packed beds and no products are withdrawn.

"SMB" refers to a simulated moving bed system.

In a continuous SMB system, all the fluid streams flow continuously. These streams are: the supply of a feed solution and an eluent, circulation of the separation profile, and withdrawal of the products.

In a sequential SMB system, all of the fluid streams (defined above) do not flow continuously.

"SAC" refers to a strongly acid cation exchange resin.

"WAC" refers to a weakly acid cation exchange resin.

"BV" refers to the resin bed volume of a partial packed bed or a column.

"A transfer fraction" refers to a fraction which contains betaine and another component (such as glycerol) as the main components and which is transferred from the SAC bed to the WAC bed.

"A replacement eluent" refers to a fraction which is collected from the SAC or WAC bed, which contains a component other than betaine (such as glycerol) as the main component, and which is used as an eluent replacement in the separation system.

"A residue fraction" or "a residual fraction" is a fraction which contains most of the components other than the product components, which are recovered. In connection with the present invention, the residue fraction is typically enriched with salts and color compounds, for example. Salts refer to cations and anions, such as $K^+$, $Na^+$, $Ca^{2+}$ and $Mg^{2+}$ and $Cl^-$, $NO_3^-$, $PO_4^{3-}$ and $SO_4^{2-}$, for example. There can be one or more residue fractions.

"A recycle fraction" is a fraction which contains incompletely separated product components, which as a rule has a lower purity than the product fractions, and which is recycled back to the separation to be combined with the feed. There may also be one or more operations before returning the recycle to the separation; for example the recycle fraction(s) may be concentrated by evaporation. There can be one or more recycle fractions.

"Volume of steps" refers to the volume of the total mobile phase (including the feed, eluent and circulation) which is moved through the separation column(s) from a predetermined step in a separation sequence to another predetermined step in the same or following sequences.

"DS" refers to the dissolved dry substance content. Equal to "dissolved solids content".

BRIEF DESCRIPTION OF THE INVENTION

An object of the present invention is to provide a method of separating betaine and at least one other component from sugar beet based fermentation solutions so as to alleviate the disadvantages related to the prior art methods, such as the problems associated with color removal and stability, tailing, and the need for high amounts of pH adjustment chemicals, as well as a high evaporation need. The objects of the invention are achieved by a method which is characterized by what is stated in the independent claim. Preferred embodiments of the invention are disclosed in dependent claims.

The invention is based on separating betaine and at least one other component from a sugar beet based fermentation solution by a combination of SAC resins (SAC bed) and WAC resins (WAC bed) in a specific order and in specified proportions in a simulated moving bed (SMB) chromatographic separation system. The chromatographic separation system is preferably a single integrated SMB system comprising both SAC and WAC beds. Alternatively, SAC and WAC beds may also be arranged as distinct separations in separate SMB systems or batch separations. In one embodiment of the invention, a fraction enriched in betaine and a fraction enriched in glycerol are collected. In a further embodiment of the invention, the fraction enriched in glycerol is circulated from the WAC bed to the SAC bed for example as an eluent replacement and glycerol is then withdrawn from the SAC bed together with other residual components. The fraction enriched in glycerol can be circulated as such without concentration. Furthermore, the process has the advantage that all components other than betaine can be withdrawn from the process in the same residual fraction.

DETAILED DESCRIPTION OF THE INVENTION

Figure 1:
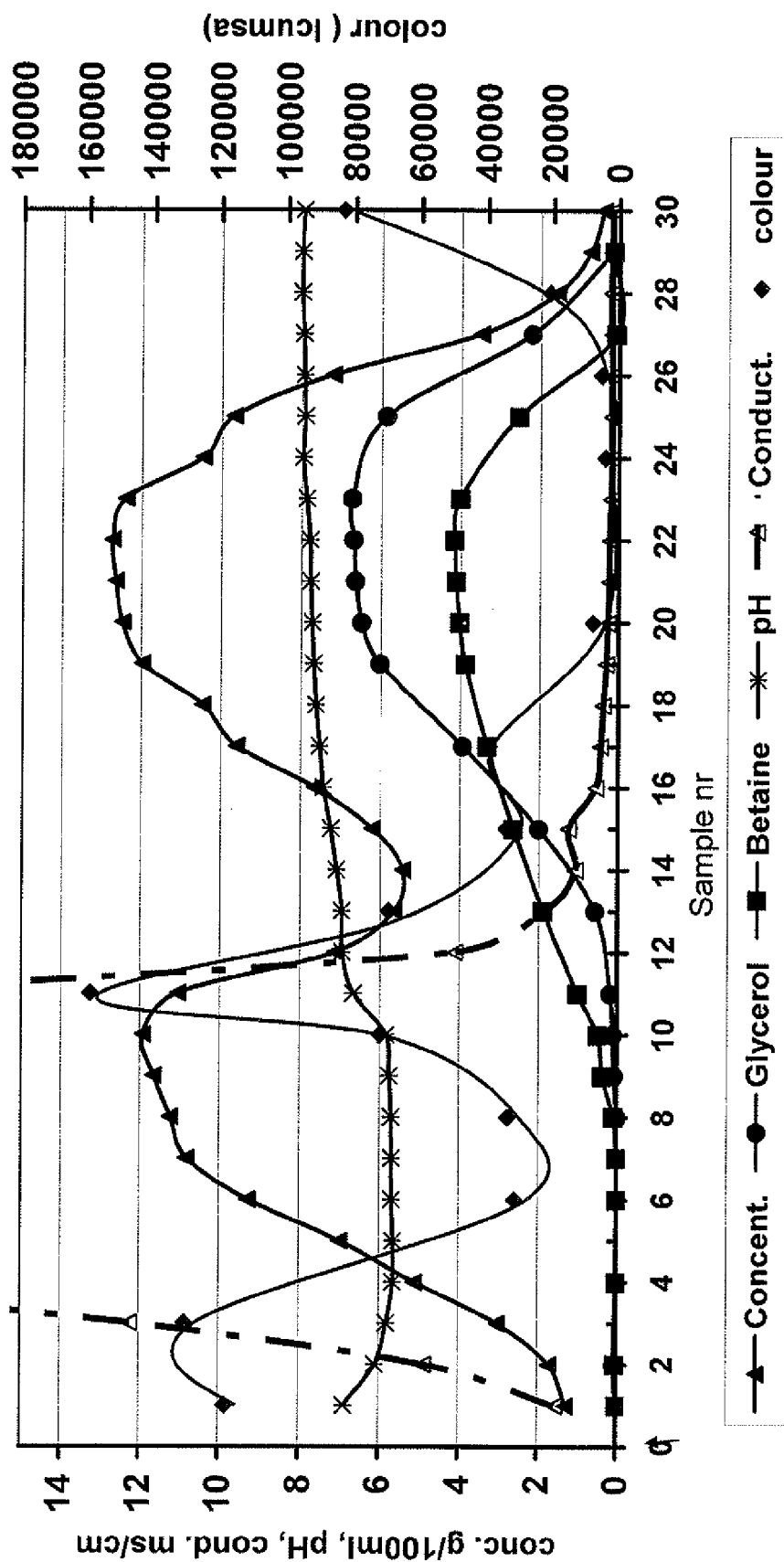
FIG. 1 depicts the separation profile of vinasse in accordance with Example 2 after the SAC bed and shows the transfer fraction from the SAC bed to the WAC bed as a part of the separation profile.
Figure 2:
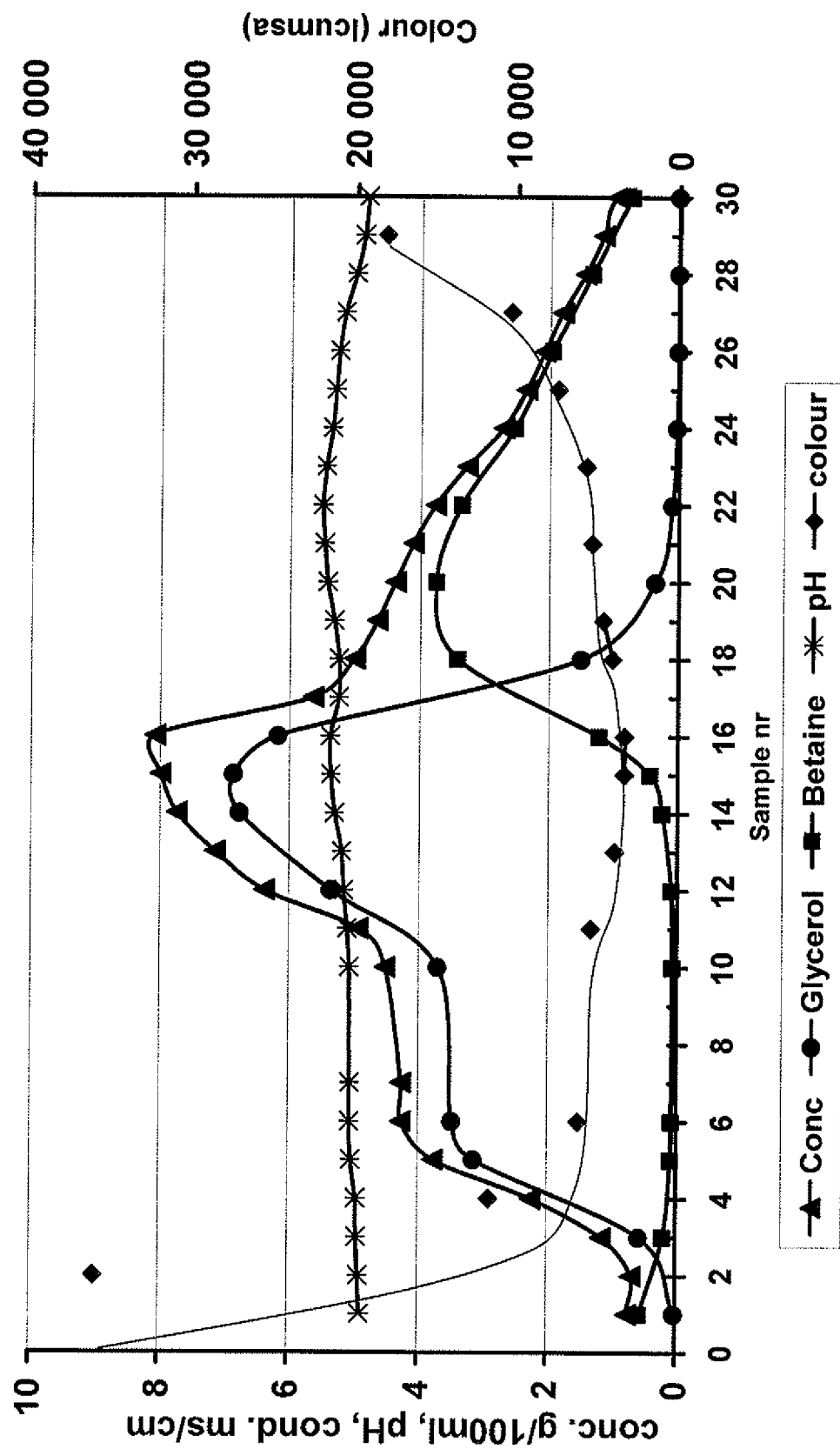
FIG. 2 depicts the separation profile of vinasse in accordance with Example 2 after the WAC bed and shows a fraction enriched in betaine and fraction enriched in glycerol.

The present invention relates to a method of separating betaine and at least one other component from a sugar beet based fermentation solution.

The method of the invention is characterized by the following features:

the separation is effected in a chromatographic SMB separation system comprising one or more partial packed beds of a strongly acid cation exchange resin and one or more partial packed beds of a weakly acid cation exchange resin, the volume of the weakly acid cation exchange resin bed(s) is 20 to 40% of the volume of the total resin bed(s) of the system, the solution is passed through the strongly acid cation exchange resin bed(s) to form a separation profile, which comprises a part of the separation profile enriched in betaine and at least one other component, and to provide a residual fraction, which is withdrawn, and said part of the separation profile enriched in betaine and at least one other component is transferred to and passed through the weakly acid cation exchange resin bed(s) to recover a fraction enriched in betaine and to provide a fraction enriched in at least one other component.

Said strongly acid cation exchange resins are typically styrenic resins crosslinked with divinylbenzene in monovalent alkali metal cation form.

In one embodiment of the invention, said strongly acid cation exchange resin is preferably a styrenic resin crosslinked with 5.5 to 8% divinylbenzene (DVB) in monovalent alkali metal cation form and has a mean particle size of 200 to 400 μm.

The separation with strongly acid cation exchange resins is preferably effected at a pH of more than 5, especially more than 5.5.

Said weakly acid cation exchange resins are typically in $H^+$ form or in monovalent alkali metal cation form. The resins may be acrylic resins crosslinked with divinylbenzene.

The weakly acid cation exchange resin may be predominantly in $H^+$ form, whereby more than 80%, preferably more than 90%, of the cations of the resin are comprised of $H^+$.

The weakly acid cation exchange resin may also be in $Na^+$ form, $K^+$ form or $Na^+/K^+$ form. When the resin is in $Na^+$ form or in $K^+$ form, more than 80%, preferably more than 90%, of the cations of the resin, are comprised of $Na^+$ or $K^+$, respectively.

The weakly acid cation exchange resin is preferably an acrylic resin crosslinked with 4 to 10% divinylbenzene (DVB) and has a mean particle size of 200 to 450 μm.

The separation with a weakly acid cation exchange resin in $H^+$ form is preferably effected at a pH of less than 4.5, while the separation with a weakly acid cation exchange resin in $Na^+$ form, $K^+$ form or $Na^+/K^+$ form is preferably effected at a pH of more than 9.

Said one or more partial packed beds of a strongly acid cation exchange resin (SAC bed) and said one or more partial packed bed(s) of a weakly acid cation exchange resin bed (WAC bed) are typically arranged in several columns.

In one embodiment of the invention, said SAC bed is arranged in four columns and said WAC bed is arranged in two columns.

In one embodiment of the invention, the fraction enriched in betaine and the fraction enriched in the other component (such as glycerol) are collected from the last column of the separation system, while residual fractions are collected from all columns.

In a preferred embodiment of the invention, the separation with the SAC bed is effected at a pH of more than 5, preferably more than 5.5, and the separation with the WAC bed is effected at a pH of less than 4.5 for $H^+$ form resin or at a pH of more than 9 for $Na^+$, $K^+$ or $Na^+/K^+$ form resin.

In the method of the present invention, the volumes of the SAC bed and the WAC bed are specified so that the volume of the WAC bed is 20 to 40% of the volume of the total resin bed(s) of the separation system. In one preferred embodiment, the volume of the WAC bed is 25 to 35% of the total resin bed. The total resin bed refers to the combined volume of the SAC bed and the WAC bed. It has been surprisingly found in accordance with the present invention that when the recited proportion are used, the separation factors of betaine and the other component in the WAC resin bed are in a correct ratio with the width of the transfer fraction moved from the SAC resin bed to the WAC resin bed to facilitate efficient separation.

The use of the WAC bed together with the SAC bed makes it also possible to operate with a shorter total bed length as compared with the use of two SAC beds, for example. The use of the WAC bed also provides improved stability of the separation system. Furthermore, pH adjustment is only needed for the transfer fraction from the SAC bed to the WAC bed, where necessary.

In the method of the present invention, the sugar beet based fermentation solution is passed through the SAC bed to form a separation profile which comprises a part of the separation profile enriched in betaine and at least one other component, and to provide a residual fraction which is withdrawn, and said part of the separation profile enriched in betaine and at least one other component is transferred to and passed through the WAC bed to recover a fraction enriched in betaine (a betaine fraction) and to provide a fraction enriched in at least one other component.

In a preferred embodiment of the invention, said part enriched in betaine and at least one other component (transfer fraction) is very low in salts (conductivity) and color as compared with the feed solution.

The volume of said part enriched in betaine and at least one other component (transfer fraction) may constitute 15 to 50% of the volume of the WAC bed to which said part is transferred.

In one embodiment of the invention, said part enriched in betaine and at least one other component is transferred to the WAC bed as a mixed transfer fraction. In this embodiment of the invention, said part is collected for example into an intermediate tank and then introduced to the WAC bed from the intermediate tank. The pH of the transfer fraction may be adjusted to a suitable value, depending on the ion form of the WAC bed. The mixed separation profile may also be a combination of several of said parts collected from the system.

In another embodiment of the invention, said part enriched in betaine and at least one other component may be transferred as an essentially intact separation profile as a direct stream from the SAC bed, comprising online pH adjustment, where necessary.

In a further embodiment of the invention, said fraction enriched in at least one other component is circulated to the SMB separation system as a replacement of an eluent by introducing it to the SAC bed. The other component is then withdrawn from the SAC bed in a residual fraction, for example.

Said at least one other component is typically withdrawn in a residual fraction simultaneously with fast moving components (such as salts) of the sugar beet based fermentation solutions, such as vinasse. This is in practice achieved by utilizing the differences in the retention volumes of salts and said other component, such as glycerol. The retention volumes of salts and glycerol may be experimentally determined for the resin beds in use. For example, as to SAC resins, the retention volume of salts is approximately 27 to 34% of the resin bed volume (BV) of the SAC bed, and the retention volume of glycerol is approximately 65 to 75% of the resin bed volume of the SAC bed.

In a further embodiment of the invention, a part of the residual fraction is circulated within the SAC bed by introducing it as an eluent replacement to the SAC bed to be eluted out during the same or following separation sequences in one or more of the residual fractions. The volume of eluent water is further reduced and the dry solids content of residual fractions will be increased.

Said circulation may be effected by introducing replacement eluent(s) to a position selected from (a) a position between successive feeds, (b) a position between successive profiles, and (c) a position in the middle of the separation profile. In one embodiment of the invention, a glycerol fraction is introduced after the betaine peak in the profile between columns 2 and 3 in a six-column system.

In one embodiment of the invention, said at least one other component is glycerol. The other component to be separated may also be selected from an organic acid and inositol. The organic acids present in the vinasse raw material may be gluconic acid, succinic acid, lactic acid, pyrrolidone carboxylic acid (PCA), and acetic acid, for example.

In one embodiment of the invention where said at least one other component is glycerol, the transfer fraction may contain almost equal amounts of betaine and glycerol, and the amount of other compounds is less than 30% on DS, preferably less than 15% on DS. The glycerol content in a circulated glycerol fraction is advantageously over 50% on DS.

In one embodiment of the invention, the glycerol fraction obtained from the WAC bed may be used as an eluent replacement as follows:

the glycerol fraction is circulated to the separation system to substitute part of the eluent, glycerol is moved forward in the separation system using a sequence of steps, which steps comprise one or more of a feeding phase, a circulation phase, and an elution phase, glycerol is withdrawn during the same or following separation sequences in one or more of the residual fractions, whereby the volume, introduction position and introduction step of the glycerol fraction are determined on the basis of the retention volume of glycerol, the volume of the resin bed through which glycerol passes, and the volume of steps moving glycerol from the introduction position to the calculated target withdrawal position during the same or following separation sequences while maintaining the high yield and purity of betaine.

In the latter embodiment of the invention, the glycerol fraction may be introduced into the elution of the next feed or feeds (sequences) in a suitable position by calculating the introduction volume and step of the glycerol fraction so that the glycerol moves in the separation profile during the next feed or feeds (sequences) to be withdrawn from the system together with salts in the salt-glycerol fraction. In practice, this is carried out by utilizing the differences in the retention volumes of salts and glycerol, as described above.

It was found that glycerol is especially useful as an eluent replacement in the separation of betaine from vinasse and other sugar beet based fermentation solutions. This is probably due to its inert properties and its retention characteristics in the separation of betaine. Especially good results are obtained when the glycerol fraction from the WAC bed is introduced into a position where glycerol does not reach betaine and is withdrawn in a residual fraction together with salts. A further advantage is that a high proportion of glycerol from the WAC bed may be used as an eluent replacement in the SAC bed. The proportion of glycerol is over 50% and preferably over 80% of the glycerol of the feed. The glycerol content in the circulated glycerol fraction is advantageously over 50% on DS.

The SMB separation in the present invention may be sequential or continuous.

In the method of the invention, the eluent is preferably water. Up to 30% of the eluent water can be replaced with the glycerol fraction. This leads to a considerable reduction in the amount of fresh eluent.

Said one or more of the partial packed beds of the separation system may form one or more separate loops during selected steps in a separation sequence in SMB.

In one embodiment of the invention, the separation system comprises a loop formed by one or more of the partial packed beds of the strongly acid cation exchange resin.

In another embodiment of the invention, the separation system comprises a loop from one or more of the partial packed beds of the weakly acid cation exchange resin to one or more of the partial packed beds of the strongly acid cation exchange resin.

The separation system may also comprise one or more separation profiles in a loop.

The sugar beet based fermentation solution used as a feed solution in the present invention is preferably vinasse, which is obtained as a residue from the fermentation of a sugar beet based material, such as molasses, into ethanol, yeast or other products.

A typical average composition of a useful vinasse raw material has a dry substance content (DS) of 50 to 70 g/100 g and is composed as follows:

| Component | % on DS |
| --- | --- |
| Betaine | 12 to 23 |
| Glycerol | 2 to 20 |
| Organic acids | 10 to 20 |
| Inorganic salts | 10 to 20 |
| Color | 100 000 ICUMSA |
| pH 5 to 6 | |

In one embodiment of the invention, the dry substance content of the feed solution is typically in a range of 30 to 50%.

In a preferred embodiment of the invention, the SAC bed and the WAC bed are arranged in a single integrated SMB system. The integrated SMB system refers to a system where the SAC bed and the WAC bed are operating under the same control program with the same separation sequence. There may also be recycle/circulation streams from the SAC bed to the WAC bed or from the WAC bed to the SAC bed.

In one embodiment of the invention, a betaine fraction and a glycerol fraction are collected from the integrated SMB system. In another embodiment of the invention, the glycerol fraction is circulated from the WAC bed to the SAC bed as a replacement of an eluent.

Consequently, one embodiment of the invention relates to a method of separating betaine and glycerol from a sugar beet based fermentation solution, which is characterized by the following features:

the separation is effected in a chromatographic SMB separation system comprising one or more partial packed beds of a strongly acid cation exchange resin and one or more partial packed beds of a weakly acid cation exchange resin, the volume of the weakly acid cation exchange resin bed(s) is 20 to 40% of the volume of the total resin bed(s) of the system, the solution is passed through the strongly acid cation exchange resin bed(s) to form a separation profile, which comprises a part of the separation profile enriched in betaine and glycerol, and to provide a residual fraction, and said part of the separation profile enriched in betaine and glycerol is transferred to and passed through the weakly acid cation exchange resin bed(s) to recover a fraction enriched in betaine (a betaine fraction) and to provide a fraction enriched in glycerol, and said fraction enriched in glycerol is circulated to the SMB separation system as a replacement of an eluent by introducing it into at least one of said one or more partial packed beds of a strongly acid cation exchange resin, and glycerol is withdrawn from said one or more partial packed beds of a strongly acid cation exchange resin.

In an alternative embodiment of the invention, the SAC bed and the WAC bed are arranged as distinct separations systems, which may be SMB or batch separations. In this alternative, the SAC bed and the WAC bed are operating under separate control programs with separate separation sequences. This embodiment of the invention may further comprise circulation of the glycerol fraction from the WAC bed to the SAC bed as a replacement of an eluent.

The method of the invention typically provides a betaine fraction with a betaine purity of more than 80%, and a betaine yield in a range of 80 to 95%, typically 80 to 90%. The betaine fraction obtained is useful as such for the crystallization of betaine.

In one embodiment, the method of the invention provides a high betaine purity and a high betaine yield together with a low W/F ratio (the ratio of the volume of eluent water to the volume of the feed). For instance, in a method comprising the circulation of the glycerol fraction, a W/F ratio as low as 1.7 can be achieved.

Furthermore, the method of the invention also reduces the color content of betaine, as compared with the WAC $H^+$ separation, for example. The color content of the betaine fraction obtained by the method of the invention is typically less than 30 000, preferably less than 15 000 ICUMSA.

The following examples illustrate the invention without limiting the invention in any way.

Example 1

Chromatographic SMB Separation of Vinasse with WAC $H^+$ (Comparative Example)

The process equipment included three columns connected in series, a feed pump, circulation pumps, an eluent water pump, heat exchangers, flow control means for out-coming liquids as well as inlet and product valves for the various process streams. The height of the columns was 4 m and each column had a diameter of 0.2 m (except the first one 0.21 m). Columns were packed with a weakly acidic gel type cation exchange resin (manufactured by Finex) in $H^+$ form. The divinylbenzene content of the resin was 8.0% and the mean bead size of the resin was 0.43 mm.

Before the separation, vinasse liquor was diluted with water to about 40 weight-% and microfiltrated with a Scepter 0.1 μm membrane. Thereafter the solution was pH-adjusted to a pH of 3.4 by using sulfuric acid (93%) and thereafter vinasse was pre-coat filtered using diatomaceous earth as a filter aid. The amount of the pre-coat was 1 kg/m², the amount of the body feed was 1.0% on DS, and the temperature was 80° C. The feed was composed as set forth below, whereby the percentages are given on a DS basis.

TABLE E1-1

Composition of the feed

| | |
|---|---|
| Feed DS, g/100 g | 39.7 |
| Betaine, % on DS | 15.8 |
| Glycerol, % on DS | 9.9 |
| Inositol, % on DS | 0.9 |
| Fructose, % on DS | 2.0 |
| Others, % on DS | 71.4 |

The fractionation was performed by way of an 8-step SMB sequence as set forth below. The aim of the separation was to separate betaine and others components contained therein. The feed and the eluent were used at a temperature of 80° C., and water was used as the eluent.

Step 1: 37.5 l of feed solution was pumped into the first column at a flow rate of 110 l/h, and a recycle fraction was collected from the third column.

Step 2: 36.0 l of feed solution was pumped into the first column at a flow rate of 65 l/h, and a residual fraction was collected from the first column. Simultaneously, 98.0 l of water was pumped into the second column at a flow rate of 180 l/h, and a betaine fraction was collected from the third column.

Step 3: 15.0 l of water was pumped into the second column at a flow rate of 125 l/h, and the outflow from column 3 was circulated into column 1, from which a residual fraction was collected.

Step 4: 37.5 l circulation in the column loop, formed with columns 1, 2 and 3, at a flow rate of 125 l/h.

Step 5: 60.0 l of water was pumped into the third column at a flow rate of 125 l/h, and the outflow from column 3 was circulated into column 1, and a residual fraction was collected from the second column.

Step 6: 35.0 l circulation in the column loop, formed with columns 1, 2 and 3, at a flow rate of 125 l/h.

Step 7: 46.0 l of water was pumped into the first column at a flow rate of 125 l/h, and a residual fraction was collected from the third column.

Step 8: 65.0 l of water was pumped into the first column, and a fraction containing glycerol and acids was collected from the third column at a flow rate of 125 l/h.

After equilibration of the system, the following fractions were drawn from the system: a residual fraction from columns 1, 2 and 3, recycle fractions from the third column, fractions containing glycerol and acids from column 3, and betaine product fractions from the third column. The results, including HPLC analyses for the combined fractions, are set forth in the table below.

TABLE E1-2

| | Combined residual | Recycle | Glycerol + acids | Betaine |
|---|---|---|---|---|
| Volume, l | 157.0 | 37.5 | 65.0 | 98.0 |
| Dry solids, g/100 ml | 10.1 | 7.3 | 15.3 | 6.0 |
| Betaine, % on DS | 0.6 | 28.2 | 0.2 | 80.0 |
| Glycerol, % on DS | 7.7 | 0.0 | 19.3 | 0.0 |
| Inositol, % on DS | 1.2 | 0.4 | 0.7 | 0.0 |
| Fructose, % on DS | 3.3 | 0.0 | 1.3 | 0.0 |
| Others, % on DS | 87.2 | 71.4 | 78.5 | 20.0 |

The overall betaine yield calculated from the combined residual fraction, the fraction containing glycerol and acids, and the betaine fraction was 97.7%. In this run, the W/F (water to feed) ratio was 3.9. When the residual fraction, the betaine fraction and the fractions containing glycerol and acids are evaporated to 60 weight-%, the condensate removal is 57.7 kg per kg betaine. The color of the betaine fraction was 158 000 ICUMSA.

Example 2

Chromatographic SMB Separation of Vinasse with a Combination of SAC in $Na^+$ Form and WAC in $H^+$ Form The process equipment included six columns connected in series, a feed pump, circulation pumps, an eluent water pump, heat exchangers, flow control means for out-coming liquids as well as inlet and product valves for the various process streams. The height of first four columns was 2 m, the height of last two columns was 1.5 m, and each column had a diameter of 0.2 m (except the first one 0.21 m). The first four columns having a total volume of 254 l were packed with a strong acid gel type cation exchange resin (manufactured by Mitsubishi) in $Na^+$ form. The divinylbenzene content of the resin was 6.0% and the mean bead size of the resin was 0.2 mm. The last two columns 5 and 6 having a total volume of 95 l and comprising 27% of the total volume of the separation system were packed with a weakly acidic gel type cation exchange resin (manufactured by Finex) in $H^+$ form. The divinylbenzene content of the resin was 8.0% and the mean bead size of the resin was 0.43 mm.

Before the separation, vinasse liquor was diluted with water to about 45 weight-% and microfiltrated with a Scepter 0.1 μm membrane. pH was adjusted to 6.0 with NaOH, and thereafter vinasse was pre-coat filtered by using diatomaceous earth as a filter aid. The amount of the pre-coat was 1 kg/m², the amount of the body feed was 0.5% on DS, and the temperature was 80° C. The feed was composed as set forth below, whereby the percentages are given on a dry substance weight basis.

TABLE E2-1

| Composition of the feed | |
|---|---|
| Feed DS, g/100 g | 42.3 |
| Betaine, % on DS | 14.9 |
| Glycerol, % on DS | 11.8 |
| Inositol, % on DS | 0.5 |
| Fructose, % on DS | 1.5 |
| Others, % on DS | 71.3 |
| pH | 5.9 |

The fractionation was performed by way of an 8-step SMB sequence as set forth below. The aim of the separation was to separate betaine and glycerol contained therein. The feed and the eluent were used at a temperature of 80° C., and water was used as the eluent.

Step 1: 7.0 l of feed solution was pumped into the first column at a flow rate of 63 l/h, and a recycle fraction was collected from the fourth column. Simultaneously, 4.0 l was circulated in the column loop, formed with columns 5 and 6, at a flow rate of 35 l/h.

Step 2: A loop was formed over all columns. 10.0 l of feed solution were pumped into the first column at a flow rate of 63 l/h, and a betaine fraction was collected from the sixth column. Simultaneously, a first portion of a part of the separation profile enriched in betaine and glycerol was transferred from the SAC bed from column 4 to the WAC bed to column 5.

Step 3: 13.0 l of feed solution was pumped into the first column at a flow rate of 63 l/h, and a residual fraction was collected from the same column. Simultaneously, 30.0 l of water was pumped into the second column at a flow rate of 95 l/h, and a residual fraction was collected from third column. In addition, 25.0 l of water was pumped into the fourth column at a flow rate of 80 l/h, and betaine was collected from the last column. Simultaneously, a second portion of a part of the separation profile enriched in betaine and glycerol was transferred from the SAC bed from column 4 to the WAC bed to column 5.

Step 4: 6.0 l of water was pumped into the second column at a flow rate of 63 l/h, and the outflow from column 4 was circulated into column 1, in which a residual fraction was collected. Simultaneously, 5.0 l circulation was started in the column loop, formed with columns 5 and 6, at a flow rate of 55 l/h.

Step 5: 11.0 l circulation in the column loop, formed with columns 1, 2, 3 and 4, at a flow rate of 63 l/h, and simultaneously, 6.0 l circulation was continued in the column loop, formed with columns 5 and 6, at a flow rate of 35 l/h.

Step 6: 6.0 l of water was pumped into the first column at a flow rate of 63 l/h, and a residual fraction was collected from the fourth column. Simultaneously, 6.0 l of water was pumped into the fifth column at a flow rate of 63 l/h, and a betaine fraction was collected from the last column.

Step 7: 20.0 l of water was pumped into the first column, and a residual fraction was collected from the second column at a flow rate of 63 l/h. Simultaneously, 20.0 l of water was pumped into the third column, and a residual fraction was collected from the fourth column at a flow rate of 63 l/h, and simultaneously, 18.0 l of water was pumped into the fifth column, and a glycerol fraction was collected from the last column at a flow rate of 55 l/h.

Step 8: 10.0 l of water was pumped into the third column having circulation from the fourth column into the first column at a flow rate of 63 l/h, and a residual fraction was collected from the second column. Simultaneously, 10.0 l of water was pumped into the fifth column at a flow rate of 63 l/h and a glycerol fraction was collected from the last column.

The volume of the WAC bed was 95 liters. The volume of the transfer fraction (a part of the separation profile enriched in betaine and glycerol) transferred from column 4 to column 5 (from the SAC bed to the WAC bed) in steps 2 and 3 was 35 l (37% of the volume of the WAC bed).

After equilibration of the system, the following fractions were drawn from the system: a residual fraction from columns 1, 2, 3 and 4, recycle fractions from the fourth column, and betaine and glycerol product fractions from the last column. The results, including HPLC analyses for the combined fractions, are set forth in the table below.

TABLE E2-2

| | Combined residual | Recycle | Glycerol | Betaine |
|---|---|---|---|---|
| Volume, l | 105.0 | 7.0 | 34.0 | 35.0 |
| Dry solids, g/100 ml | 10.8 | 13.9 | 5.4 | 5.3 |
| Betaine, % on DS | 1.0 | 48.9 | 6.0 | 80.2 |
| Glycerol, % on DS | 0.6 | 22.7 | 67.6 | 8.5 |
| Inositol, % on DS | 0.04 | 1.2 | 3.0 | 0.0 |
| Fructose, % on DS | 0.14 | 5.0 | 7.5 | 0.2 |
| Others, % on DS | 98.2 | 22.3 | 15.9 | 11.1 |
| pH | 5.5 | 6.9 | 4.6 | 5.3 |

The overall betaine yield calculated from these fractions was 86.8% and the glycerol yield was 84.5%. In the run, all residual was taken out from the system without circulation, and the W/F (water to feed) ratio was 5.1. When the residual, betaine and glycerol fractions are evaporated to 60 weight-%, the condensate removal is 103.1 kg per kg betaine. The color of the betaine fraction was 13000 ICUMSA.

Example 3

Chromatographic SMB Separation of Vinasse with a Combination of SAC in $Na^+$ Form and WAC in $H^+$ Form—Glycerol Fraction Circulated The process equipment included six columns connected in series, a feed pump, circulation pumps, an eluent water pump, heat exchangers, flow control means for out-coming liquids as well as inlet and product valves for the various process streams. The height of first four columns was 2 m, the height of last two columns was 1.5 m, and each column had a diameter of 0.2 m (except the first one 0.21 m). The first four columns (having a total volume of 254 l) were packed with a strong acid gel type cation exchange resin (manufactured by Mitsubishi) in Na$^+$ form. The divinylbenzene content of the resin was 6.0%, and the mean bead size of the resin was 0.2 mm. The last two columns 5 and 6 (having a total volume of 95 l, which comprises 27% of the total volume of the separation system) were packed with a weakly acidic gel type cation exchange resin (manufactured by Finex) in H$^+$ form. The divinylbenzene content of the resin was 8.0%, and the mean bead size of the resin was 0.43 mm.

The pretreatment of vinasse liquor was similar to that described in Example 2. The feed was composed as set forth below, whereby the percentages are given on a DS basis.

TABLE E3-1

Composition of the feed

| | |
|---|---|
| Feed dry substance, g/100 g | 37.8 |
| Betaine, % on DS | 15.9 |
| Glycerol, % on DS | 12.5 |
| Inositol, % on DS | 0.5 |
| Fructose, % on DS | 1.7 |
| Others, % on DS | 69.4 |
| pH | 5.1 |

The fractionation was performed by way of a 10-step SMB sequence as set forth below. The aim of the separation was to separate betaine and to recycle glycerol back to the SAC separation in order to reduce eluent water consumption as well as to get most of the glycerol to be eluted out in residual fractions. The feed and the eluent were used at a temperature of 80° C., and ion exchanged water was used as the eluent.

Step 1: 7.0 l of feed solution was pumped into the first column at a flow rate of 65 l/h, and a recycle fraction was collected from the fourth column. Simultaneously, 4.0 l was circulated in the column loop, formed with columns 5 and 6, at a flow rate of 40 l/h.

Step 2: 10.0 l of feed solution was pumped into the first column at a flow rate of 65 l/h, and a recycle fraction was collected from the sixth column. Simultaneously, a first portion of a part of the separation profile enriched in betaine and glycerol was transferred from the SAC bed from column 4 to the WAC bed to column 5.

Step 3: 9.0 l of feed solution was pumped into the first column at a flow rate of 65 l/h, and a residual fraction was collected from the third column. Simultaneously, 8.0 l of water was pumped into the fourth column at a flow rate of 40 l/h, and a betaine fraction was collected from the last column. Simultaneously, a second portion of a part of the separation profile enriched in betaine and glycerol was transferred from the SAC bed from column 4 to the WAC bed (to column 5).

Step 4: The first column was on hold during this step. 8.0 l of feed solution was pumped into the second column at a flow rate of 65 l/h, and a residual fraction was collected from the third column. Simultaneously, 4.0 l of water was pumped into the fourth column at a flow rate of 65 l/h, and a betaine fraction was collected from the last column. Simultaneously, a portion of a part of the separation profile enriched in betaine and glycerol was transferred from the SAC bed from column 4 to the WAC bed to column 5.

Step 5: 4.0 l of feed solution was pumped into the first column at a flow rate of 40 l/h, and a residual fraction was collected from the same column. Simultaneously, 13.0 l of water was pumped into second column, and a betaine fraction was collected from the last column. Simultaneously, a portion of a part of the separation profile enriched in betaine and glycerol was transferred from the SAC bed from column 4 to the WAC bed to column 5.

Step 6: 6.0 l of water were pumped into the second column having a circulation loop from the fourth column into the first column at a flow rate of 65 l/h, and a residual fraction was collected from the first column. Simultaneously, 5.0 l circulation was started in the column loop, formed with columns 5 and 6, at a flow rate of 55 l/h.

Step 7: 11.0 l circulation in the column loop, formed with columns 1, 2, 3 and 4, at a flow rate of 65 l/h, and simultaneously, 6.0 l circulation was continued in the column loop, formed with columns 5 and 6, at a flow rate of 35 l/h.

Step 8: 6.0 l of water was pumped into the fifth column at a flow rate of 65 l/h, and a glycerol fraction was circulated from column 6 to column 1 to be used as a replacement eluent, and a residual fraction was collected from the fourth column.

Step 9: 20.0 l of water was pumped into the fifth column at a flow rate of 65 l/h, and a glycerol fraction was circulated from column 6 to column 1 to be used as a replacement eluent, and a residual fraction was collected from the second column. Simultaneously, 20.0 l of water was pumped into the third column, and a residual fraction was collected from the fourth column at a flow rate of 65 l/h.

Step 10: 10.0 l of water was pumped into the fifth column at a flow rate of 65 l/h, and a glycerol fraction from column 6 was circulated to column 3 to be used as a replacement eluent, and the outflow from column 4 was circulated into column 1, and a residual fraction was collected from the second column.

The volume of the WAC bed was 95 liters. The volume of the transfer fraction (a part of the separation profile enriched in betaine and glycerol) transferred from column 4 to column 5 (from the SAC bed to the WAC bed) in steps 2, 3, 4, and 5 was 35 l (37% of the volume of the WAC bed).

After equilibration of the system, the following fractions were drawn from the system: a residual fraction from columns 1, 2, 3 and 4, recycle fractions from the fourth column and a betaine product fraction from the last column. The results, including HPLC analyses for the combined fractions, are set forth in the table below.

TABLE E3-2

| | Combined residual | Recycle | Betaine |
|---|---|---|---|
| Volume, l | 83.0 | 17.0 | 25.0 |
| Dry solids, g/100 ml | 12.9 | 8.4 | 5.3 |
| Betaine, % on DS | 2.6 | 41.4 | 85.0 |
| Glycerol, % on DS | 8.9 | 38.0 | 6.4 |
| Inositol, % on DS | 0.5 | 1.2 | 0.2 |
| Fructose, % on DS | 1.3 | 5.5 | 0.3 |
| Others, % on DS | 86.7 | 14.0 | 8.3 |

The overall betaine yield calculated from these fractions was 80.0%. The glycerol fraction from the WAC resin bed was introduced into columns between the feeds (steps 8 and 9) and profiles (step 10) to be withdrawn in residual fractions together with salts. About 60% of glycerol (calculated from the fractions of Table E3-2) was withdrawn in residual fractions and 35% of glycerol was withdrawn in a recycle fraction. Altogether about 95% of glycerol of the feed was withdrawn from the SAC columns of the SMB system. The volume of the residual fractions was further reduced and the dry solids content was increased by circulating a part of the residual fractions from columns 1 and 3 in order to make them elute simultaneously with the residual fractions of the following profile(s). Only residual and betaine fractions were taken out from the system, and the W/F (water to feed) ratio was 3.2. When the residual and betaine fractions are evaporated to 60 weight-%, the condensate removal is 81.4 kg per kg betaine. The evaporation demand was reduced 21% when compared with the test run described in Example 2 without the circulation of the glycerol fraction as an eluent.

Example 4

Comparative Example with Two Separate Chromatographic Separations

A. Chromatographic SMB Separation of Vinasse with SAC $Na^+$-Form

The process equipment included four columns connected in series, a feed pump, circulation pumps, an eluent water pump, heat exchangers, flow control means for out-coming liquids as well as inlet and product valves for the various process streams. The height of each column was 2.0 m, and each column had a diameter of 0.2 m (except the first one 0.21 m). The columns were packed with a strong acid gel type cation exchange resin (manufactured by Finex) in $Na^+$ form. The divinylbenzene content of the resin was 7.5% and the mean bead size of the resin was 0.328 mm.

Before the separation, vinasse liquor was diluted with water to 40-45 weight-% and microfiltrated by using a Scepter 0.1 μm membrane. pH of the vinasse liquor was adjusted to 6.3 with 32 w-% NaOH and filtrated further with a Seitz pressure filter. The concentration of the feed solution was adjusted to 34 g/100 ml. The feed was composed as set forth below, whereby the percentages are given on a DS basis.

TABLE E4-1

| Composition of the feed | |
|---|---|
| Feed DS, g/100 g | 30.2 |
| Betaine, % on DS | 15.8 |
| Glycerol, % on DS | 15.2 |
| Inositol, % on DS | 0.5 |
| Fructose, % on DS | 1.9 |
| Others, % on DS | 66.7 |

The fractionation was performed by way of a 9-step SMB sequence as set forth below. The aim of the separation was to separate betaine and glycerol from most salts and other compounds with reduced water consumption. The feed and the eluent were used at a temperature of 80° C., and ion exchanged water was used as the eluent.

Step 1: This step was not in use.

Step 2: 4.7 l of feed solution was pumped into the first column at a flow rate of 63 l/h, and an eluent replacement fraction was collected from the third column. Simultaneously, 2.5 l of water was pumped into the last column at a flow rate of 35 l/h, and a betaine-glycerol fraction was collected from the last column.

Step 3: 15.0 l of feed solution was pumped into the first column at a flow rate of 63 l/h, and a residual fraction was collected from the same column. Simultaneously, 10.5 l of water was pumped into second column at a flow rate of 44 l/h, and a betaine-glycerol fraction was collected from the last column.

Step 4: 10.7 l of feed solution was pumped into the first column at a flow rate of 63 l/h, and a betaine-glycerol fraction was collected from the last column.

Step 5: 9.3 l circulation in the column loop, formed with columns 1, 2, 3 and 4, at a flow rate of 63 l/h.

Step 6: 14.0 l circulation in the column loop, formed with columns 1 and 2, at a flow rate of 63 l/h. Simultaneously, 14.0 l of water was pumped into the third column at a flow rate of 63 l/h, and a residual fraction was collected from the last column.

Step 7: 4.7 l of the eluent replacement fraction collected from column 3 as described in step 2 was pumped into the first column at a flow rate of 63 l/h, and a residual fraction was collected from the second column. Simultaneously, 6.0 l of water was pumped into the third column at a flow rate of 80 l/h, and a residual fraction was collected from the last column.

Step 8: 4.0 l of water was pumped into the first column at a flow rate of 63 l/h, and a residual fraction was collected from the second column. Simultaneously, 4.0 l of water was pumped into the third column at a flow rate of 63 l/h, and a residual fraction was collected from the last column.

Step 9: 21.0 l circulation in the column loop, formed with columns 1, 2, 3 and 4, at a flow rate of 63 l/h.

After equilibration of the system, the following fractions were drawn from the system: a residual fraction from columns 1, 2 and 4, an eluent replacement fraction from the third column and a glycerol-containing betaine product fraction from the last column. The results, including HPLC analyses for the combined fractions, are set forth in the table below.

TABLE E4-2

| | Combined residual | Eluent replacement | Betaine-glycerol |
|---|---|---|---|
| Volume, l | 47.7 | 4.7 | 23.7 |
| Dry solids, g/100 ml | 14.7 | 5.5 | 13.3 |
| Betaine, % on DS | 0.4 | 0.5 | 46.5 |
| Glycerol, % on DS | 1.9 | 1.0 | 41.3 |
| Inositol, % on DS | 0.1 | 0.1 | 1.2 |
| Fructose, % on DS | 0.3 | 0.2 | 5.1 |
| Others, % on DS | 97.4 | 98.3 | 6.0 |

The overall betaine yield calculated from these product fractions was 97.9%, and the color of the betaine-glycerol fraction was 29 100 ICUMSA. Only the residual and betaine fractions were taken out from the system, and the W/F (water to feed) ratio was 1.35. When the residual fraction was evaporated to 60 weight-% and the betaine-glycerol fraction was evaporated to 30 weight-%, the condensate removal was 35.6 kg per kg betaine.

B. Chromatographic Batch Separation of the Betaine-Glycerol Fraction with WAC in $Na^+$ Form The process equipment included a laboratory scale batch column provided with a heat jacket, feed and eluent water tanks, an outflow pump, thermostated water baths, flow control means for out-coming liquid as well as inlet valves for the feed and eluent water. The height of the resin bed was 1.5 m, and the diameter of the column was 0.093 m. The column was packed with a weakly acidic gel type cation exchange resin (manufactured by Finex) in $Na^+$ form. The divinylbenzene content of the resin was 8.0% and the mean bead size of the resin was 0.28 mm.

The betaine-glycerol fraction obtained in accordance with Example 4A was used as a feed solution. The feed solution and eluent water were pH-adjusted to a pH of 9 and filtrated prior to separations. The flow rate was 2.94 l/h and feed size 0.9 l. The feed was composed as set forth below, whereby the percentages are given on a dry substance weight basis.

TABLE E4-3

| Composition of the feed | |
|---|---|
| Feed DS, g/100 g | 30.1 |
| Betaine, % on DS | 45.3 |
| Glycerol, % on DS | 43.6 |
| Others, % on DS | 11.1 |
| pH | 9 |

The aim of the separation was to separate betaine and other compounds contained therein. The feed and the eluent were used at a temperature of 80° C., and water was used as an eluent.

After equilibration of the system, profile samples were collected at three-minute intervals, and the composition of samples was analyzed by HPLC. The separation profile was then divided into following fractions: a residual fraction, a glycerol fraction, and a betaine product fraction. The results, including HPLC analyses for the computational combined fractions, are set forth in the table below.

TABLE E4-4

| | Combined residual | Betaine | Glycerol |
|---|---|---|---|
| Volume, l | 1.5 | 1.5 | 1.4 |
| Dry solids, g/100 ml | 1.8 | 8.8 | 10.3 |
| Betaine, % on DS | 27.9 | 88.0 | 2.4 |
| Glycerol, % on DS | 0.4 | 4.2 | 82.0 |
| Others, % on DS | 71.7 | 7.8 | 15.6 |

The overall betaine yield calculated from the residual fraction, the glycerol fraction and the betaine fraction was 91.3%. In the WAC Na$^+$ run, the W/F (water to feed) ratio was 3.9. When the residual, betaine, and glycerol fractions are evaporated to 60 weight-%, the condensate removal is 34.3 kg per kg betaine. The color of the betaine fraction was 5600 ICUMSA.

The total betaine recovery calculated over this two-step separation process was 89.4%, and the W/F ratio was 2.5. When the evaporation needs between the separation steps and in the end are calculated, the total condensate removal was 69.9 kg per kg betaine.

Example 5

Chromatographic SMB Separation of Vinasse with SAC Na$^+$ and WAC Na$^+$ Combination The process equipment included six columns connected in series, a feed pump, circulation pumps, an eluent water pump, three break tanks, heat exchangers, flow control means for out-coming liquids as well as inlet and product valves for the various process streams. There was a pH adjustment with NaOH in the break tank No. 1, and the target value was 9.0. The height of the resin beds in all columns was 2.0 m, and each column had a diameter of 0.2 m and a volume of 63 l (except the first one 0.21 m, volume 69 l). The first four columns were packed with a strong acid cation (SAC) gel type exchange resin (manufactured by Finex) in Na$^+$ form. The divinylbenzene content of the resin was 7% and the mean bead size of the resin was 0.33 mm. The last two columns, 5 and 6, were packed with a weak acid cation (WAC) gel type exchange resin (manufactured by Finex) in Na$^+$ form. The divinylbenzene content of the resin was 8%, and the mean bead size of the resin was 0.31 mm.

Before the separation, vinasse was diluted with water and microfiltrated with a Scepter 0.1 μm filter. pH was adjusted to 6.3 with NaOH, and after this vinasse was pre-coat filtered using diatomaceous earth as a filter aid. The amount of the pre-coat was 1 1kg/m$^2$, the amount of the body feed was 1.0% on dissolved solids (DS), and the temperature was 80° C. The feed composition is presented in Table E5-1, where the percentages are given on a DS basis.

TABLE E5-1

| Composition of the feed | |
|---|---|
| Feed DS, g/100 g | 30 |
| Betaine, % on DS | 18.7 |
| Glycerol, % on DS | 17.9 |
| Inositol, % on DS | 0.5 |
| Fructose, % on DS | 1.9 |
| Others, % on DS | 61.0 |

The fractionation was an 8-step SMB sequence as set forth below. The aim of the chromatographic separation was to separate betaine from vinasse with a reduced eluent water consumption. Reductions in eluent water usage can be achieved by circulating selected fractions from columns back to other columns. In this example, the greatest benefit was achieved by circulating a fraction from the WAC columns into the SAC columns (a break tank in between). The feed and the eluent were used at a temperature of 80° C., and ion exchanged water was used as the eluent.

Step 1: 4.7 l of the feed solution was pumped into the first column at a flow rate of 63 l/h, and a residual fraction was collected from the third column. Simultaneously, 1.5 l of water was pumped to the fourth column at a flow rate of 40 l/h, and an out-coming fraction (transfer fraction) was collected into break tank No. 1, which was used as a feed tank from the SAC columns to the WAC columns (columns 5 and 6). Simultaneously, 5.1 l of a betaine-glycerol rich fraction from break tank No. 2 was pumped to the fifth column at a flow rate of 68 l/h, and a betaine fraction was collected from the sixth column.

Step 2: 15.0 l of the feed solution was pumped to the first column at a flow rate of 63 l/h, and a residual fraction was collected from the same column. Simultaneously, 10.5 l water was pumped to the second column at a flow rate of 44 l/h, and the out-coming fraction (transfer fraction) was collected from the fourth column into break tank No 1. In addition, 2.2 l of a replacement eluent fraction from break tank No. 2 was pumped to the fifth column at a flow rate of 10 l/h, and a WAC recycle fraction was collected from the sixth column to the break tank No. 2.

Step 3: 10.7 l of feed solution was pumped to the first column at a flow rate of 63 l/h, and the out-coming fraction from the fourth column (transfer fraction) was collected into break tank No. 1. Simultaneously, 5.1 l of water was pumped into the fifth column at a flow rate of 30 l/h, and a betaine-glycerol rich fraction was collected from the sixth column into break tank No. 2.

Step 4: 11.3 l was circulated in the column loop, formed of columns 1 1 to 4 at a flow rate of 63 l/h. In addition, 20.1 l of water was pumped into the fifth column at a flow rate of 112 l/h, and a glycerol-enriched fraction was collected from the sixth column into break tank No. 3.

Step 5: 5.4 l circulation in the column loop, formed of the columns 1 and 2, was started at a flow rate of 63 l/h. Simultaneously, a first portion of the glycerol-enriched fraction, 9.0 l from break tank No. 3, was pumped as an eluent to the third column, and a residual fraction was collected from the fourth column. In addition, 0.6 l of water was pumped to the fifth column at a flow rate of 7.0 l/h, and a residual fraction was collected from the sixth column.

Step 6: 6.6 l circulation in the column loop formed of the columns 1 and 2 at a flow rate of 63 l/h was continued. Simultaneously, the rest of the glycerol enriched fraction, 11.1 l, from break tank No. 3 was pumped into the third column at a flow rate of 105 l/h, and a residual fraction was collected from the fourth column. There was no flow in the columns 5 and 6.

Step 7: 8.7 l of water was pumped into the first column and a residual fraction was collected from the second column at a flow rate of 63 l/h. Simultaneously, 5.4 l of water was pumped into the third column, and a residual fraction was collected from the fourth column at a flow rate of 39 l/h. In addition, 3.8 l of transfer fraction from break tank No. 1 was pumped to the fifth column, and a residual fraction was collected from the last column at a flow rate of 27 l/h.

Step 8: 20.0 l was circulated in the column loop, formed of columns 1 to 4 at a flow rate of 63 l/h. Simultaneously, the rest of the transfer fraction, 18.9 l, from break tank No. 1, was pumped to the fifth column, and a betaine fraction was collected from the last column at a flow rate of 59 l/h.

The volume of the WAC bed was 33% (126 liters) of the total resin bed volume of the separation system. The volume of the transfer fraction (a part of the separation profile enriched in betaine and glycerol) collected from column 4 of the SAC bed in steps 1, 2, and 3 was 22.7 liters. After adjusting the pH to 9, this transfer fraction was introduced to column 5 in steps 7 and 8. The volume of the transfer fraction was 18% of the volume of the WAC bed.

After equilibration of the system, the following fractions were drawn from the system: a residual fraction from columns 1, 2, 3, 4 and 6, as well as a glycerol-enriched fraction, a betaine-glycerol fraction from the WAC bed and replacement eluent and betaine fractions from the last column. The results, including HPLC analyses for the combined fractions, are set forth in the table below.

TABLE E5-2

|  | Combined residual fraction | Transfer fraction (tank No. 1) | Betaine-glycerol rich fraction (tank No. 2) | Glycerol enriched fraction (tank No. 3) | Betaine fraction |
|---|---|---|---|---|---|
| Volume, l | 58.3 | 22.7 | 7.3 | 20.1 | 24.0 |
| pH | 6.1 | 9.6 | 8.9 | 8.2 | 8.6 |
| Dry solids, g/100 ml | 15.3 | 17.2 | 14.0 | 11.0 | 7.7 |
| Betaine, % on DS | 3.8 | 47.0 | 57.9 | 12.2 | 80.8 |
| Glycerol, % on DS | 18.2 | 43.1 | 41.8 | 64.4 | 8.4 |
| Inositol, % on DS | 0.2 | 1.0 | 0.2 | 0.4 | 1.1 |
| Fructose, % on DS | 2.0 | 4.5 | — | 6.6 | 0.6 |
| Others, % on DS | 75.8 | 4.4 | — | 16.4 | 9.1 |
| Color, ICUMSA |  |  |  |  | 12200 |

Approximately 90% of glycerol (calculated on the withdrawn fractions) is eluted in the residual fractions from the SAC columns. The overall betaine yield calculated from these fractions was 82.5%. When the betaine fraction is evaporated to 60 weight-%, the condensate removal is 43.0 kg/kg betaine. Only residual and betaine fractions were taken out from the system, and the W/F (water to feed, vol/vol) ratio was 1.7.

It will be obvious to a person skilled in the art that, as technology advances, the inventive concept can be implemented in various ways. The invention and its embodiments are not limited to the examples described above but may vary within the scope of the claims.

The invention claimed is:

1. A method of separating betaine and at least one other component from a sugar beet based fermentation solution in a chromatographic SMB separation system comprising one or more partial packed beds of a strongly acid cation exchange resin and one or more partial packed beds of a weakly acid cation exchange resin, wherein the volume of the weakly acid cation exchange resin bed(s) is 20 to 40% of the volume of the total resin bed(s) of the system, comprising
passing the solution through the strongly acid cation exchange resin bed(s) to form a separation profile, which comprises a part of the separation profile enriched in betaine and at least one other component, and to provide a residual fraction, which is withdrawn, and
transferring and passing said part of the separation profile enriched in betaine and at least one other component to and through the weakly acid cation exchange resin bed(s) to recover a fraction enriched in betaine and to provide a fraction enriched in at least one other component.

2. The method as claimed in claim 1, wherein said strongly acid cation exchange resin is a styrenic resin crosslinked with 5.5 to 8% divinylbenzene (DVB) in a monovalent alkali metal cation form and has a mean particle size of 200 to 400 μm.

3. The method as claimed in claim 2, wherein the separation is effected at a pH of more than 5.

4. The method as claimed in claim 1, wherein said weakly acid cation exchange resin is in $H^+$ form.

5. The method as claimed in claim 4, wherein more than 80% of the cations of the weakly acid cation exchange resin are comprised of $H^+$.

6. The method as claimed in claim 1, wherein the weakly acid cation exchange resin is in $Na^+$ form, $K^+$ form or $Na^+/K^+$ form.

7. The method as claimed in claim 6, wherein more than 80% of the cations of the resin are comprised of $Na^+$ or $K^+$, respectively.

8. The method as claimed in claim 4, wherein the resin is an acrylic resin crosslinked with 4 to 10% divinylbenzene (DVB) and has a mean particle size of 200 to 450 μm.

9. The method as claimed in claim 4, wherein the separation is effected at a pH of less than 4.5.

10. The method as claimed in claim 6, wherein the separation is effected at a pH of more than 9.

11. The method as claimed in claim 1, wherein said one or more partial packed beds of a strongly acid cation exchange resin and said one or more partial packed beds of a weakly acid cation exchange resin are arranged in several columns.

12. The method as claimed in claim 11, wherein said one or more partial packed beds of a strongly acid cation exchange resin are arranged in four columns and said one or more weakly acid cation exchange resin beds are arranged in two columns.

13. The method as claimed in claim 1, wherein the separation with one or more partial packed beds of a strongly acid cation exchange resin is effected at a pH of more than 5, and
the separation with one or more partial packed beds of a weakly acid cation exchange resin is effected at a pH of less than 4.5 for $H^+$ form resin or at a pH of more than 9 for $Na^+$, $K^+$ or $Na^+/K^+$ form resin.

14. The method as claimed in claim 1, wherein the volume of said part enriched in betaine and at least one other component constitutes 15 to 50% of the volume of the weakly acid cation exchange resin bed(s).

15. The method as claimed in claim 1, wherein said part enriched in betaine and at least one other component is transferred as a mixed transfer fraction.

16. The method as claimed in claim 1, wherein said fraction enriched in at least one other component is circulated to the SMB separation system as a replacement of an eluent by introducing it to at least one of said one or more partial packed beds of a strongly acid cation exchange resin, and said at least one other component is withdrawn from said one or more partial packed beds of a strongly acid cation exchange resin.

17. The method as claimed in claim 16, wherein said at least one other component is withdrawn in a residual fraction.

18. A method as claimed in claim 1, a part of the residual fraction is circulated within said one or more partial packed beds of a strongly acid cation exchange resin by introducing it as an eluent replacement to said one or more partial packed beds of a strongly acid cation exchange resin.

19. The method as claimed in claim 16, wherein said circulation is effected by introducing said fraction to a position selected from (a) a position between successive feeds, (b) a position between successive profiles, and (c) a position in the middle of the separation profile.

20. The method as claimed in claim 16, wherein the eluent is water, and up to 30% of the eluent water is replaced by said fraction enriched in at least one other component or by said part of the residual fraction.

21. The method as claimed in claim 1, wherein the other component to be separated is glycerol.

22. The method as claimed in claim 1, wherein the other component to be separated is selected from an organic acid and inositol.

23. The method as claimed in claim 1, wherein said one or more partial packed beds of the separation system form one or more separate loops.

24. The method as claimed in claim 23, wherein the separation system comprises a loop formed by the partial packed bed(s) of the strongly acid cation exchange resin.

25. The method as claimed in claim 23, wherein the separation system comprises a loop from the partial packed bed(s) of a weakly acid cation exchange resin to the partial packed bed(s) of a strongly acid cation exchange resin.

26. The method as claimed in claim 1, wherein the sugar beet based fermentation solution is vinasse.

27. The method as claimed in claim 1, wherein the dry substance content of the feed solution of the separation system is 30 to 50%.

28. A method of separating betaine and glycerol from a sugar beet based fermentation solution,
in a chromatographic SMB separation system comprising one or more partial packed beds of a strongly acid cation exchange resin and one or more partial packed beds of a weakly acid cation exchange resin, wherein
the volume of the weakly acid cation exchange resin bed(s) is 20 to 40% of the volume of the total resin (beds) of the system,
passing the solution through the strongly acid cation exchange resin bed(s) to form a separation profile, which comprises a part of the separation profile enriched in betaine and glycerol, and to provide a residual fraction, and
transferring and passing said part of the separation profile enriched in betaine and glycerol to and through the weakly acid cation exchange resin bed(s) to recover a betaine fraction and to provide a fraction enriched in glycerol, and
circulating said fraction enriched in glycerol to the SMB separation system as a replacement of an eluent by introducing it to at least one of said one or more partial packed beds of a strongly acid cation exchange resin, and withdrawing glycerol from said one or more partial packed beds of a strongly acid cation exchange resin.

29. The method as claimed in claim 2, wherein the separation is effected at a pH of more than 5.5.

30. The method as claimed in claim 4, wherein more than 90% of the cations of the weakly acid cation exchange resin are comprised of H+.

31. The method as claimed in claim 6, wherein more than 90% of the cations of the resin are comprised of $Na^+$ or $K^+$, respectively.

32. The method as claimed in claim 6, wherein the resin is an acrylic resin crosslinked with 4 to 10% divinylbenzene (DVB) and has a mean particle size of 200 to 450 μm.

33. The method as claimed in claim 13, wherein the separation with one or more partial packed beds of a strongly acid cation exchange resin is effected at a pH of more than 5.5.

34. The method as claimed in claim 18, wherein said circulation is effected by introducing said fraction to a position selected from (a) a position between successive feeds, (b) a position between successive profiles, and (c) a position in the middle of the separation profile.

35. The method as claimed in claim 18, wherein the eluent is water, and up to 30% of the eluent water is replaced by said fraction enriched in at least one other component or by said part of the residual fraction.

* * * * *